US00PP36337P2

(12) United States Plant Patent
van Kessel

(10) Patent No.: US PP36,337 P2
(45) Date of Patent: Dec. 24, 2024

(54) ***SARRACENIA* PLANT NAMED '23CF202'**

(50) Latin Name: *Sarracenia purpurea*
Varietal Denomination: 23CF202

(71) Applicant: Carni Flora B.V., Aalsmeer (NL)

(72) Inventor: Justin van Kessel, Aalsmeer (NL)

(73) Assignee: Carni Flora BV (NL)

( * ) Notice: Subject to any disclaimer, the term of this patent is extended or adjusted under 35 U.S.C. 154(b) by 0 days.

(21) Appl. No.: 18/661,955

(22) Filed: May 13, 2024

(51) Int. Cl.
*A01H 5/12* (2018.01)
*A01H 6/00* (2018.01)

(52) U.S. Cl.
USPC ..... Plt./477

(58) Field of Classification Search
USPC ..... Plt./477
See application file for complete search history.

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of *Sarracenia* plant named '23CF202' is disclosed, characterized by a unique dark red pitcher hood, which turns darker in the summer to nearly black. Pitchers have a pronounced visible netting of both the pitcher and hood. Plants are distinctly compact. The new variety is a *Sarracenia*, with uses as both an indoor and outdoor ornamental plant.

3 Drawing Sheets

Latin name of the genus and species: *Sarracenia purpurea.*

Variety denomination: '23CF202'.

BACKGROUND OF THE INVENTION

This application relates to a new cultivar of *Sarracenia*. The new variety is the product of a planned breeding program to develop distinct, better performing new *Sarracenia* varieties. The seed parent is *Sarracenia purpurea venosa*, the species itself. The pollen parent is the unpatented *Sarracenia purpurea* #2020, of the breeder's own selection. The crossing resulting in the new variety was made in 2017, at a nursery in Aalsmeer, the Netherlands.

*Sarracenia* '23CF202' was selected by the inventor as an interesting new cultivar in 2020 at the same nursery in Aalsmeer, the Netherlands.

Asexual reproduction of the new cultivar '23CF202' was first performed at a tissue lab in the Netherlands by tissue culture in April of 2020. Through subsequent asexual propagation, approximately 4 generations have been reproduced, which have shown that the unique features of this cultivar are stable and reproduced true to type.

SUMMARY OF THE INVENTION

The cultivar '23CF202' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of '23CF202.' These characteristics in combination distinguish '23CF202' as a new and distinct *Sarracenia* cultivar:

1. Dark red color of the hood and pitcher, even darker in summer (almost black).
2. Compact growth habit.
3. Pronounced visible netting of the pitcher and hood.

PARENT COMPARISONS

Plants of the new cultivar '23CF202' are similar to the seed parent variety, in many horticultural characteristics. However, the new variety, '23CF202' differs in the following characteristics:

1. The young pitcher of the new variety is green, quickly changing color to dark red. The young pitcher of the seed parent is greener, and changes color later.
2. The pitcher of the new variety is less pointed, more round than the pitcher of the seed parent.

Plants of the new cultivar '23CF202' are similar to the pollen parent variety, in many horticultural characteristics. However, the new variety, '23CF202' differs in the following characteristics:

1. Pitchers of the new variety are much more compact than the pitchers of the pollen parent.
2. Pitchers of the new variety are more round than pitchers of the pollen parent.

COMMERCIAL COMPARISONS

The new variety can be compared to the unnamed, unpatented commercial variety *Sarracenia purpurea* var. *purpurea*. However, the new variety, '23CF202' differs in the following characteristics:

1. Pitchers of the new variety are slightly longer than pitchers of this comparator.
2. Plants of the new variety grow much more quickly than plants of this comparator.
3. Plant habit of the new variety is more open, while the plant habit of this comparator is more compact.
4. Pitchers of the new variety mature more quickly than pitchers of this comparator.

'23CF202' can be compared with the commercial variety *Sarracenia purpurea* spp. *venosa* 'Burkii', unpatented. However, the new variety, '23CF202' differs in the following characteristics:

1. The hood of the new variety remains more upright with a slight bend, while the hood of this comparator bends more over the pitcher's mouth.
2. Pitchers and hoods of the new variety turn almost black in summer, while pitchers and hoods of this comparator turn dark red in summer.
3. The hood of the new variety is heart-shaped, while hoods of this comparator has a more "waved" shape.
4. Pitchers of the new variety are less thick and swollen than pitchers of this comparator.

BRIEF DESCRIPTION OF THE PHOTOGRAPHS

The accompanying photograph in FIG. 1 illustrates in full color a typical plant of '23CF202' grown in a glass greenhouse in Aalsmeer, the Netherlands. The plant is in a 12-cm pot, approximately one year old.

Figure 1:
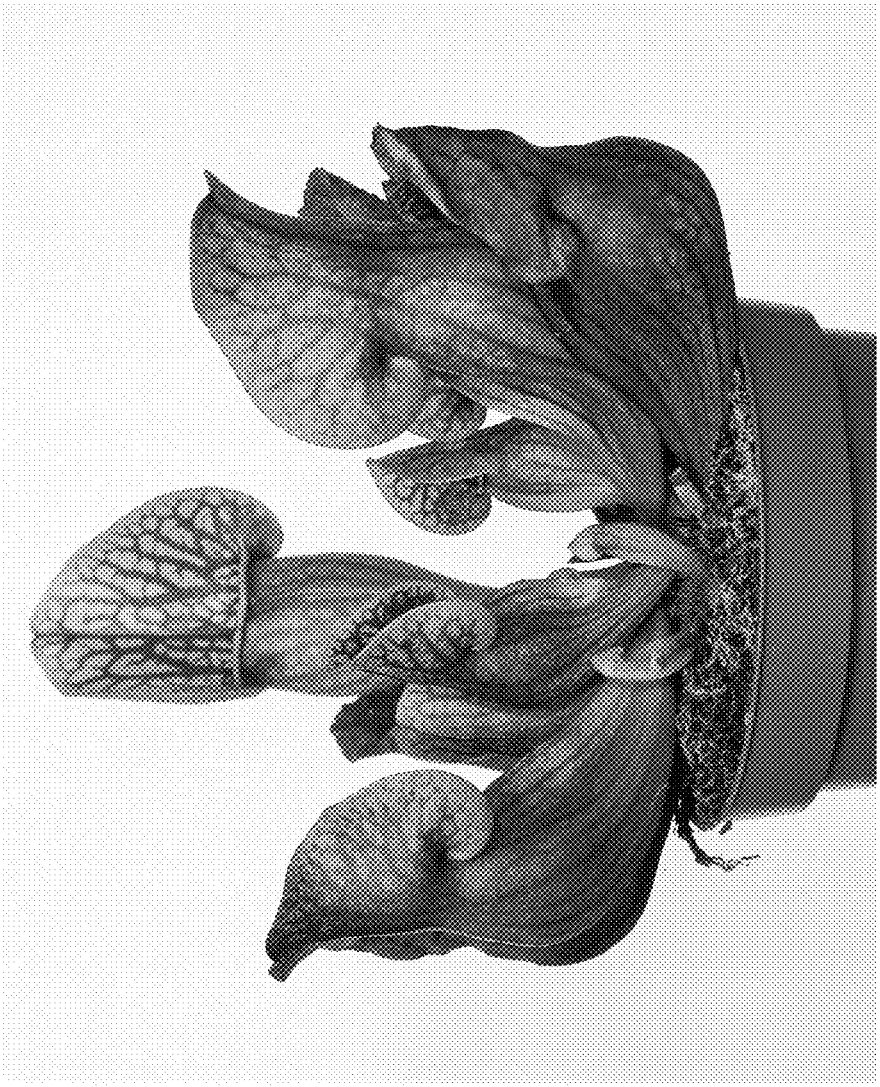
Figure 2:
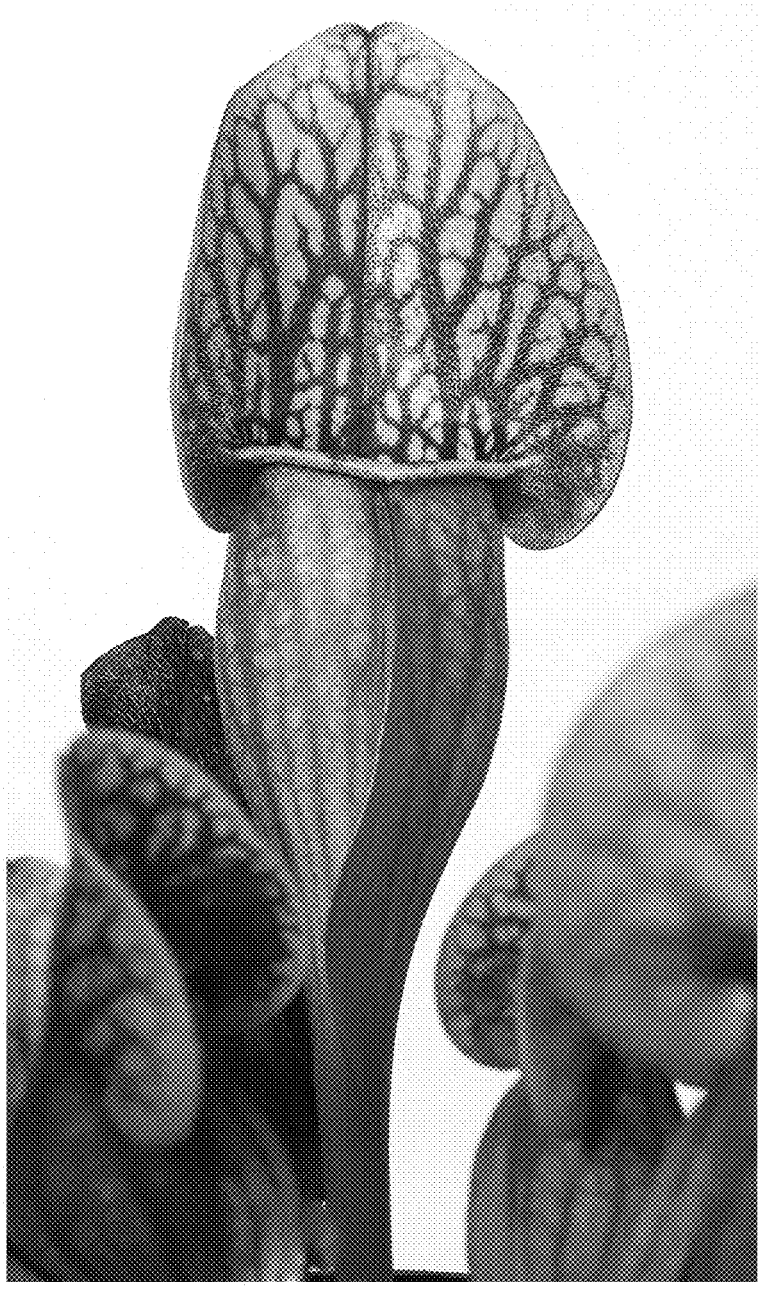
FIG. 2 illustrates an immature pitcher.
Figure 3:
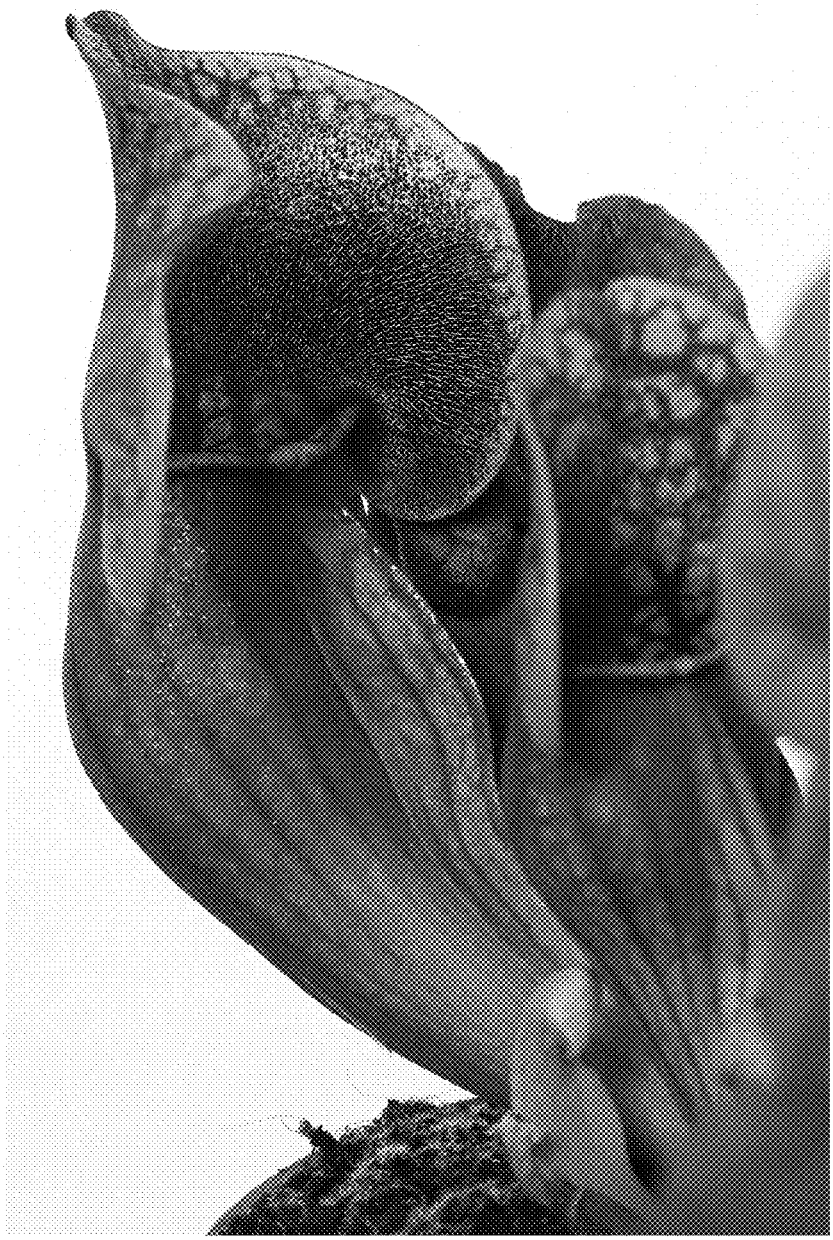
FIG. 3 illustrates a fully mature pitcher.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe '23CF202' plant is grown in a glass greenhouse in Aalsmeer, the Netherlands. The plant is approximately one year old in a 12-cm pot. Temperatures ranged between 21° C. to 35° C. during the day and 19° C. to 21° C. at night. No chemical treatments were given to the plants. Measurements and numerical values represent averages of typical plant types.

Botanical classification: *Sarracenia purpurea* '23CF202'.

PROPAGATION

Time to initiate rooting: 30 days at 24° C. in summer; 40 days at 20° C. in winter.

Root description: Shallow, smooth, hairy. Average diameter: 1 mm. Sparse to moderately dense. Colored RHS Greyed-Yellow 161A and 161B.

PLANT

Plant type: Perennial potted plant.

Growth habit: Broad spreading-upright, with epiascidiate leaves growing from a basal rosette.

Height: Approximately 15 cm.

Plant spread: Approximately 18.7 cm.

Plant vigor: Moderate.

Growth rate: Low to moderate.

Branching habit: Epiascidiate leaves growing from a basal rosette, no branches present.

FOLIAGE

Leaf:

*Arrangement*.—Alternate, single, in basal rosette.

*Quantity*.—Average 17 leaves per plant.

*Length*.—Average: 14.1 cm. Lower leaf zone (tube) average: 10 cm. Upper leaf zone (lid) average: 6.2 cm.

*Width*.—Lower leaf zone (tube) average diameter: 3.5 cm. Upper leaf zone (container) average: 7.5 cm.

*Shape*.—Leaf epiascidiate, typically consisting of a lower leaf zone, with a lamina rolled into a tube with a ventral wing and an upper leaf zone, formed as lid. Lower leaf zone shaped tubular, upper leaf zone (lid) shaped cordate.

*Aspect*.—Leaves in an average angle of 20° to horizontal, curled upward to 90° (near vertical) at the tip.

*Apex*.—Retuse to shallow emarginate.

*Base*.—Tubular, fused.

*Margin*.—Lower leaf zone tubular, ventral wing entire. Upper leaf zone (lid) entire, coarsely undulate.

*Texture*.—Top surface: Lower leaf zone (tube) and upper leaf zone (lid): smooth, glabrous. Bottom surface: Lower leaf zone (tube) and upper leaf zone (lid): smooth, pubescent.

*Pubescence*.—Upper side of upper leaf zone (tube): Moderately covered with very short adpressed strigose hairs; average length: 1.25 mm, colored near RHS White NN155D. Under side of lower leaf zone (tube): Densely covered with very short soft hairs; average length shorter than 0.2 mm, colored white; impossible to measure with RHS-CC due to small size. Under side of upper leaf zone (lid): Moderately to densely covered with very short soft hairs; average length: 0.4 mm, colored white; impossible to measure with RHS-CC due to small size.

*Rugosity*.—Lower leaf zone (tube) and upper leaf zone (lid) non-rugose on both sides.

*Luster*.—Upper side: Lower leaf zone (tube): Glossy. Upper leaf zone (lid): Slightly glossy. Under side: Lower leaf zone (tube): Very slightly glossy. Upper leaf zone (lid): Very slightly glossy.

*Color*.—Young foliage, upper side: Lower leaf zone (tube): RHS Yellow-Green 146D reticulately veined Greyed-Purple 185A towards the top. Upper leaf zone (lid): RHS Yellow-Green 144B to 144C, reticulately veined Greyed-Purple 183A. Young foliage, under side: Lower leaf zone (tube): RHS Yellow-Green 144B and 146D, reticulately veined Greyed-Purple 183B to 183D towards the top. Upper leaf zone (lid): RHS Yellow-Green 152B to 152C, reticulately veined Greyed-Purple; 183B and 183C, main vein nearest 185A. Mature foliage, upper side: Lower leaf zone (tube): RHS Yellow-Green 144B, fading to Greyed-Red 182A to 182D towards the top. Upper leaf zone (lid): RHS Greyed-Purple 187A, margined Yellow-Green 144B. Mature foliage, under side: Lower leaf zone (tube): RHS Yellow-Green 145A, tinged Greyed-Orange 176B, particularly towards the top. Upper leaf zone (lid): RHS Yellow-Green 144B, margined 143B, strongly blotched and tinged Greyed-Purple 183B.

*Venation*.—Type: Reticulate. Color: Mature foliage, upper side: Lower leaf zone (tube): RHS Greyed-Purple 183B to 183D. Upper leaf zone (lid): RHS Greyed-Purple 187A at margins. Mature foliage, under side: Lower leaf zone (tube): RHS Greyed-Purple 184A to 184C. Upper leaf zone (lid): RHS Greyed-Purple 183B.

Other distinguishing characteristics: Lower leaf zone (tube) of epiascidiate leaves with a ventral wing, average length 8.8 cm, average width: 1.3 cm, texture and color similar to lower leaf zone (tube).

OTHER CHARACTERISTICS

Fruit/seed production: No fruits/seeds detected to date.

Temperature tolerance: Unknown, at least tolerant from −10° C. to 35° C.

USDA hardiness zones: USDA zones 4 to 9.

Tolerance to rain: High.

Tolerance to wind: Moderate.

Disease and pest resistance or tolerance: Neither resistant nor susceptible to normal diseases and pests of *Sarracenia*.

What is claimed is:

1. A new and distinct cultivar of *Sarracenia* plant named '23CF202' as herein illustrated and described.

* * * * *